United States Patent
Liao et al.

(10) Patent No.: US 10,821,207 B2
(45) Date of Patent: Nov. 3, 2020

(54) COMPOSITE MATERIALS FOR BONE REPAIR BASED ON DECELLULARIZED BIOLOGICAL TISSUE MATRIX MATERIAL AND THE PREPARATION METHOD THEREOF

(71) Applicant: Hangzhou Huamai Medical Devices Co., Ltd., Binjiang District, Hangzhou, Zhejiang (CN)

(72) Inventors: Hua Liao, Hubei (CN); Chunhua Yu, Zhejiang (CN); Tao Jiang, Zhejiang (CN); Xiaohua Yu, Zhejiang (CN)

(73) Assignee: Hangzhou Huamai Medical Devices Co., Ltd., Hangzhou (CN)

( * ) Notice: Subject to any disclaimer, the term of this patent is extended or adjusted under 35 U.S.C. 154(b) by 0 days.

(21) Appl. No.: 15/763,007

(22) PCT Filed: Nov. 21, 2016

(86) PCT No.: PCT/CN2016/106558
§ 371 (c)(1),
(2) Date: Mar. 23, 2018

(87) PCT Pub. No.: WO2017/097104
PCT Pub. Date: Jun. 15, 2017

(65) Prior Publication Data
US 2018/0289862 A1    Oct. 11, 2018

(30) Foreign Application Priority Data

Dec. 7, 2015    (CN) .......................... 2015 1 0895007

(51) Int. Cl.
| | | |
|---|---|---|
| *A61L 27/36* | (2006.01) | |
| *A61L 27/40* | (2006.01) | |
| *A61L 27/56* | (2006.01) | |
| *A61L 27/58* | (2006.01) | |
| *A61L 27/46* | (2006.01) | |
| *A61L 27/44* | (2006.01) | |

(52) U.S. Cl.
CPC ............ *A61L 27/40* (2013.01); *A61L 27/365* (2013.01); *A61L 27/3633* (2013.01); *A61L 27/3687* (2013.01); *A61L 27/3691* (2013.01); *A61L 27/446* (2013.01); *A61L 27/46* (2013.01); *A61L 27/56* (2013.01); *A61L 27/58* (2013.01); *A61L 2400/16* (2013.01); *A61L 2430/02* (2013.01); *A61L 2430/40* (2013.01)

(58) Field of Classification Search
CPC ......... A61L 27/40; A61L 27/36; A61K 27/58; A61K 27/56
See application file for complete search history.

(56) References Cited

U.S. PATENT DOCUMENTS

| | | |
|---|---|---|
| 7,998,499 B2 | 8/2011 | Li et al. |
| 8,303,967 B2 | 11/2012 | Clineff et al. |
| 8,460,686 B2 | 6/2013 | Clineff et al. |
| 2008/0187571 A1 | 8/2008 | Clineff et al. |
| 2009/0112317 A1 | 4/2009 | Li et al. |
| 2013/0059011 A1 | 3/2013 | Clineff et al. |
| 2014/0255489 A1 | 9/2014 | Shi |
| 2015/0065947 A1 | 3/2015 | Wallace et al. |
| 2015/0343117 A1 | 12/2015 | Ling et al. |
| 2016/0199540 A1 | 7/2016 | Liu et al. |

FOREIGN PATENT DOCUMENTS

| | | |
|---|---|---|
| CN | 101417145 A | 4/2009 |
| CN | 101417151 A | 4/2009 |
| CN | 103055352 A | 4/2013 |
| CN | 103341206 A | 10/2013 |
| CN | 103432627 A | 12/2013 |
| CN | 105412989 A | 3/2016 |
| WO | WO-00/07639 A1 | 2/2000 |
| WO | WO-2013/059089 A1 | 4/2013 |
| WO | 2017097104 A1 | 6/2017 |

OTHER PUBLICATIONS

State Intellectual Property Office of the P.R. China; PCT International Search Report, Issued in Connection to PCT/CN2016/106558; dated Mar. 7, 2017; 8 pages; China.
State Intellectual Property Office of the P.R. China; PCT Written Opinion of the International Searching Authority, Issued in Connection to PCT/CN2016/106558; dated Mar. 7, 2017; 4 pages; China.
State Intellectual Property Office of the P.R. China; First Office Action issued in connection to CN21510895007.9; dated Nov. 1, 2017; 6 pages; China.
International Search Report EP 16872297 dated Apr. 29, 2019.

(Continued)

*Primary Examiner* — Zohreh A Fay
(74) *Attorney, Agent, or Firm* — Blank Rome LLP (57) ABSTRACT

A composite material for bone repair based on a decellularized biological tissue matrix material and a preparation method thereof. The composite material for bone repair comprises an organic phase of a microfibrillar decellularized animal tissue matrix material and an inorganic phase of a calcium salt bioceramic or other inorganic bioglass. A preparation process for the composite material for bone repair does not need physical or chemical crosslinking. The composite material for bone repair has a three-dimensional porous network structure, and protein components in the biological tissue matrix material maintain a natural triplex structure. The composite material for bone repair has excellent biocompatibility, biodegradability, osteoconductivity, osteoinductivity, and osteogenecity, also has certain mechanical strength and shape memory function, and can be used as a bone filling material or a repair material for large-area bone defect.

9 Claims, 6 Drawing Sheets

(56) References Cited

OTHER PUBLICATIONS

Ehab Kheir et al. "Development and Characterization of an Acellular Porcine Cartilage Bone Matrix for Use in Tissue Engineering", Journal of Biomedical Materials Research Part A, vol. 99A, No, Nov. 19, 2011, pp. 283-294.

Crapo et al., "An Overview of Tissue and Whole Organ Decellularization Processes" Biomaterials, Elsevier Science Publishers BB., Barking, GB, vol. 32, No. 12, Jan. 19, 2011, pp. 3233-3243.

Benders et al. "Extracellular Matrix Scaffolds for Cartilage and Bone Regeneration" Trends in Biotechnology, Elsevier Publications, Cambridge, GB, V. 31, No. Jan. 5, 2013, pp. 169-176.

Harley et al. "In vivo and in vitro Applications of Collagen-GAG Scaffold", Chemical Engineering Journal, Elsevier, Amsterdam, NL, vol. 137, No. 1, Feb. 13, 2008, pp. 102-121.

結合組織の定義と分類 Definition and classification of connective tissue, 2008, URL:www.kms.ac.jp/~anatomy2/Histology6.pdf, p. 1-32.

たらしい皮膚科学 Hiroshi Shimizu, Textbook of modern dermatology, 2011, edition 2, p. 13-16.

Gu Xian Yi Shin "Composite material for Bone Repair Based on Accellular Tissue Matrix and Its Preparation" Jun. 27, 2019.

Dermis, Chapter 1 pp. 13-17.

COMPOSITE MATERIALS FOR BONE REPAIR BASED ON DECELLULARIZED BIOLOGICAL TISSUE MATRIX MATERIAL AND THE PREPARATION METHOD THEREOF

CROSS-REFERENCE TO RELATED APPLICATION(S)

This application is a 35 U.S.C. § national application of International Patent Application No. PCT/CN2016/106558, filed Nov. 21, 2016, which designated the United States and was entitled "BONE REPAIR REUSABLE COMPOSITE MATERIAL BASED ON ACELLULAR BIOLOGICAL TISSUE MATRIX MATERIAL AND PREPARATION METHOD THEREFOR," and claims priority to Chinese Patent Application No. 201510895007.9, filed on Dec. 7, 2015, the disclosures of which are incorporated by reference herein in their entirety.

TECHNICAL FIELD

The present invention belongs to the field of materials science, in particular relates to composite materials for bone repair based on decellularized biological tissue matrix material and the preparation method thereof. The composite materials can be widely used in the fields of orthopaedics and plastic surgery.

BACKGROUND

The repair and reconstruction of the impaired bone tissue are important tasks that the orthopaedic surgeons need to face all over the world. According to the statistics, over 600,000 and 1,000,000 cases of bone transplantation surgeries were performed in China and U.S.A. in 2013 respectively, and the sales of bone graft substitute materials in the world have exceeded 2 billion U.S. dollars. Bone graft materials are needed in the repair of impaired bone tissue. Autologous bone tissues, i.e., healthy bone tissues harvested from the patient's own body, have been considered worldwide the golden standard for the repair of impaired bone tissues. The autologous bone has all the properties required for repairing bone tissues, such as excellent osteoinductivity, osteoconductivity, osteogenecity and safety. However, there are clinically unavoidable drawbacks associated with the use of autologous bone. Since bone tissues need to be harvested from a donor-site of the patient's body when using autologous bone, this additional surgery will increase the duration and cost of the surgery, and the recovery time for patients. In the meantime, donor site morbidity and limited supply are other problems associated with autologous bone. In addition, the quality of bone tissues of elderly patients who need bone grafts decreases with age; therefore autologous bone is probably not a good choice for the elderly. Accordingly, the development of bone regenerative materials (or bone graft substitute materials) which can replace autologous bone is an urgent problem to be solved.

The bone graft substitute materials used clinically by orthopaedic surgeons include allogeneic bone, decalcified bone matrix, growth factors and synthetic materials. Allogeneic bone derives from a bone tissue donated by other people. It possesses osteoconductivity and is in relatively adequate supply. However, the drawbacks associated with allogeneic bone include uncontrollable quality of donor tissue, tissue rejection, long time for bone union or even nonunion, and risks of disease transmission. The decalcified bone matrix is obtained by decalcifying an allogeneic bone or a heterogeneous bone (an animal bone tissue). It is osteoconductive and is in adequate supply. There are relatively sufficient data on the clinical use of the decalcified bone matrix. Nevertheless, osteoinductivity of decalcified bone matrix material is very limited, and the use thereof also has risks of disease transmission. The growth factors for bone repair such as bone morphogenetic protein-2 (BMP-2) or bone morphogenetic protein-7 (BMP-7 or OP-1) possess osteoinductivity. However, the U.S. Food and Drug Administration (FDA) has only approved a few types of orthopaedic medical devices that contain growth factors for clinical use and sale in U.S., for example, the InFuse® (containing BMP-2) from Medtronic and OP-18 (containing BMP-7) from Stryker. Furthermore, the growth factors per s'e don't possess osteoconductivity and are very expensive. In the meantime, recently more and more clinical reports have revealed that the use of growth factors has carcinogenic risks.

Because of various unavoidable disadvantages existing in the clinical use of autologous bone, allogeneic bone, decalcified bone matrix and growth factors, synthetic materials have increasingly become the choice of orthopaedic surgeons. The synthetic bone graft materials used clinically by orthopaedic surgeons can be classified roughly into the first generation of synthetic materials and the second generation of synthetic materials. The first generation and the second generation of synthetic materials have good osteoconductivity, and are generally used as bone filling materials for repairing small area of bone defects. The first generation of synthetic materials includes various types of ceramic materials, such as tricalcium phosphate, hydroxyapatite, or composite materials of ceramic, calcium and phosphate salt with organic materials such as natural and synthetic polymers. Such types of products in the international market include Vitoss® of Stryker, MasterGraft® of Medtronic, ProOsteon® of Biomet, Healos® of DePuy, CopiOs® of Zimmer, etc. Such products do not possess osteoinductivity and osteogenecity. The second generation of synthetic materials exhibits limited function of stimulating new bone formation by introducing inorganic components with bio-activity, such as bioglass, silicon and phosphate salt and the like. The second generation of synthetic materials in the international market includes Vitoss® BA from Stryker, ActiFuse® from Baxter and NovaBone® from NovaBone. There are only a few domestic manufacturers in China developing and commercializing, bone graft substitute materials. For example, Shanghai Rebone Biomaterials Co., Ltd. produces its artificial bone materials made of self-setting calcium phosphate. Beijing Yierkang Bioengineering Development Center commercializes the ReLive® nano-artificial bone developed by Tsinghua University. The bone graft substitute materials produced by domestic manufacturers essentially belong to the first generation of synthetic materials as defined by the international classification standard.

Bone tissue is the only connective tissue which forms mineralized extracellular matrix in vertebrates. The mineralized extracellular matrix provides the hardness and strength required for skeleton. The bone matrix is consisted of both organic and inorganic components. The organic components represent about 20% of wet weight of skeleton, and the inorganic components represent about 65% of wet weight of skeleton. The organic component of the skeleton is mainly collagen, which represents about 90% of the organic components and is mainly type I collagen. With respect to the spatial structure, the collagen exhibits a special intertwining structure of triple helix. Three collagen peptide chains independent of each other maintain the intertwining structure of triple helix via the hydrogen bonds formed between glycines. This structure imparts a stable structure and excellent strength to collagen. The inorganic components of the skeleton are mainly hydroxyapatite. In order to simulate the structure and performance of bone tissue, scientists often use type I collagen, ceramic materials, or the composite materials thereof as the materials for bone repair in scientific research and clinical product development. In the current international medical device market and in the clinic, almost all collagen-containing materials for bone repair use chemically purified type I collagen. Many U.S. patents, such as U.S. Pat. Nos. 5,776,193, 5,681,872, 6,764,517, 7,189,263, 7,998,499, 8,303,967, 8,460,686 U.S. Pat. Nos. 8,968,797, 8,613,938, etc., all relate to bone repair materials mainly using chemically purified type I collagen as raw material. The clinical products transformed from these patents include Healos®, Vitoss® and Vitoss®BA and the like. Many similar domestic patents report the composite materials of chemically purified collagen and ceramics, such as CN 1338315, CN 1526765, CN 102085392, CN 103055352, CN 103341206, etc. The disadvantages of chemically purified collagen are that: the extraction process thereof is complex, and the collagen is denatured and loses its intrinsic triple helix structure during extraction, resulting in the loss of its original biological performances. In addition, the collagen is extracted from biological tissues through chemical method, resulting in that many kinds of organic components in the original biological matrix are lost in the final material, rendering that the collagen has a relatively simple composition and cannot satisfy the requirements for complex signal pathway during bone repair. In the meantime, when chemically purified collagen is used as the bone repair material, the chemical crosslinking agents with relatively high toxicity, such as formaldehyde, 2,3-dihydroxy propanal, glutaraldehyde or carbodiimide and the like, are needed to crosslink the collagen molecules so as to increase the strength and heat stability of collagen. However, after the in vivo implantation of materials and during the degradation and absorption process thereof, the small molecular crosslinking agents are released from the chemically crosslinked collagen, generate cytotoxicity and induce inflammation and immune-reaction. In order to address this underlying problem, the Chinese patent CN 101417145 reports a scaffold material for bone tissue engineering, which is prepared by obtaining a natural three-dimensional network structure of collagen from decellularized and degreased porcine skin and compounding a hydroxyapatite layer thereon, without using additional chemical crosslinking agent to crosslink collagen. This method for producing scaffold material is based on the three-dimensional network structure of collagen. Therefore, it is only limited to be used in the method wherein the mineralization is performed in calcium phosphate solution for producing the composite material of collagen and hydroxyapatite.

SUMMARY OF THE INVENTION

The object of the present invention is to provide a composite material for bone repair based on decellularized biological tissue matrix material and the preparation method thereof. The composite materials prepared by the present invention are based on decellularized biological tissue matrix. The produced biological tissue matrix material maintains a natural cross-linking state of organic components, and thus chemical crosslinking agents are not needed. The biological tissue matrix material used in the present invention has a microfibrillar shape, and thus can be used to prepare homogeneously dispersed composite material by means of physically mixing the matrix material with inorganic materials such as calcium phosphate and the like or by means of biomineralization.

The objects of the present invention are achieved by the following technical solutions:

A composite material for bone repair based on decellularized biological tissue matrix material comprises 10%-90% of a decellularized biological tissue matrix material as organic phase and 90%-10% of a calcium salt as inorganic phase.

Preferably, the calcium salt is replaced by bioglass, bioceramic, mineral containing strontium, zinc, magnesium or silicon or salt containing strontium, zinc, magnesium or silicon as the inorganic phase.

Preferably, the inorganic phase as a dispersed phase is distributed in form of particles within the organic phase as a continuous phase: the inorganic phase can be distributed homogeneously in the organic phase, or distributed with a certain gradient in the organic phase.

Preferably, the composite material for bone repair based on decellularized biological tissue matrix material has a three-dimensional porous network structure.

Preferably, the decellularized biological tissue matrix material derives from soft tissue of mammals. The soft tissue of mammals comprises a soft tissue of pig, a soft tissue of bovine and a soft tissue of human body. The soft tissue comprises skin, dermis, blood vessel, diaphragm, muscle tendon, ligament, large intestine, small intestine and nervous tissue.

Preferably, the decellularized biological tissue matrix material has a microfibrillar shape. The microfibrillar decellularized biological tissue matrix material has a diameter of 1-250 micrometers and a length of 100-4000 micrometers.

Preferably, the calcium salt is hydroxyapatite [$Ca_5(PO_4)_3OH$], α-tricalcium phosphate [$α-Ca_3(PO_4)_2$], β-tricalcium phosphate [$β-Ca_3(PO_4)_2$]) calcium hydrophosphate [$CaHPO_4$], calcium hydrophosphate dihydrate [$CaHPO_4 \cdot 2H_2O$], calcium dihydrogenphosphate [$Ca(H_2PO_4)_2$], tetracalcium phosphate [$Ca_4(PO_4)_2O$], octacalcium phosphate [$Ca_8H_2(PO_4)_6 \cdot 5H_2O$], calcium sulfate [$CaSO_4$] or calcium carbonate [$CaCO_3$].

A preparation method of the composite material for bone repair comprises the following steps:

1.1) preparing a microfibrillar decellularized biological tissue matrix material, comprising the following steps:

(a) collecting raw tissue material, rinsing off blood, cutting into desired size, and preserving the material at a low temperature of 2-10° C.;

(b) disinfecting and sterilizing: sterilizing the raw tissue material in a disinfectant solution, washing sufficiently with sterile deionized water, and then rinsing with a sterile physiological saline;

(e) cutting: cutting the raw tissue material into desired size, so as to facilitate tissue smashing and decellularization;

(d) smashing the tissue: smashing and homogenizing the disinfected raw tissue material by a grinder;

(e) soaking the material in a series of decellularization solutions to remove cells, and degrading the remaining desoxyribonucleic acid with deoxyribonuclease solution;

(f) washing the tissue matrix: washing the product in step (e) by physiological saline with a mass concentration of 0.9%, and removing the supernatant obtained via the treatment of step (e) by centrifugation process;

(g) terminally sterilizing: dispersing the product in step (f) into a solvent of a physiological saline or a phosphate buffer saline at a concentration of 10-40 mg/ml, sterilizing, and sealing the obtained decellularized biological tissue matrix microfibers in a closed container to preserve;

1.2) preparing bioceramic microparticles, comprising the following steps:

(h) obtaining bioceramic microparticles with a particle size of 1-500 micrometers after the steps of mechanical pulverization, high-rate ball-milling, and sieving of the bioceramics according to specific application, and then disinfecting and sterilizing the bioceramic microparticles under high temperature and high pressure to inactivate virus;

(i) mixing the bioceramic microparticles with sterile physiological saline, sufficiently stirring and shocking to obtain a homogeneous suspension with a concentration of 500-1000 mg/ml;

1.3) preparing the composite material for bone repair, comprising the following steps:

(j) physically mixing the microfibrillar decellularized biological tissue matrix material obtained in (g) of step 1.1) with the sterile particulate bioceramic produced in (i) of step 1.2) homogeneously according to the ratio defined in the present invention, to obtain a mixture of composite material in a fluid state;

(k) transferring the mixture of composite material in (j) of step 1.3) into a mold, placing the mold filled with the composite material at a temperature of $-20°$ C. to $-196°$ C. for 1-24 hours to obtain a frozen mixture;

(l) removing the solvent from the mixture at a frozen state obtained in (k) of step 1.3) at a low temperature of $-20°$ C. to $10°$ C. and under a vacuum environment of 10-2000 millitorr for 12-96 hours, resulting in a three-dimensional porous composite material for bone repair;

(m) terminally sterilizing the composite material for bone repair obtained in (l) of step 1.3).

As an alternative, the preparation method of composite materials for bone repair comprises the following steps:

2.1) preparing a microfibrillar decellularized biological tissue matrix material according to step 1.1) of the method described above;

2.2) preparing the composite materials for bone repair, comprising following steps:

(a) transferring the decellularized biological tissue matrix material in step 2.1) into a mold, placing the mold filled with the material at a temperature of $-20°$ C. to $-196°$ C. for 1-24 hours to obtain a frozen biological tissue matrix material;

(b) removing the solvent from the biological tissue matrix material at a frozen state obtained in (a) of step 2.2) at a low temperature of $-20°$ C. to $10°$ C. and under a vacuum environment of 10-2000 millitorr for 12-96 hours, obtaining a three-dimensional porous biological tissue matrix material;

(c) soaking the three-dimensional porous biological tissue matrix material obtained in (b) of step 2.2) in a solution containing calcium ion at 20-37° C. for 1-4 hours, then taking out the biological tissue matrix material and washing with deionized water three times, 5 minutes each time; soaking the biological tissue matrix material in a solution containing phosphate ion at 20-37° C. for 1-4 hours, then taking out the biological tissue matrix material and washing with deionized water three times, 5 minutes each time; the molar ratio of the addition amount of the calcium ion to that of the phosphate ion is Ca/P=1/1 to 2/1; repeating the above steps for 5 times to obtain a three-dimensional porous composite material for bone repair;

(d) terminally sterilizing the composite material for bone repair obtained in (c) of step 2.2).

Preferably, the raw material derives from soft tissue of mammals. The soft tissue of mammals comprises a soft tissue of pig, a soft tissue of bovine and a soft tissue of human body. The soft tissue comprises skin, dermis, blood vessel, diaphragm, muscle tendon, ligament, large intestine, small intestine and nervous tissue.

The advantageous technical effects of the present invention are as follows.

The composite materials prepared by the present invention show superior bone repair performance to the typical bone repair materials on the international medical device market and in clinical use, such as Healon® from Johnson & Johnson and Vitoss® BA from Stryker. Currently, all of these types of bone repair materials involving biological agents in the clinic use chemically purified type I collagen. The disadvantages of this type of collagen are that: the extraction process thereof is complex, and the collagen is denatured during extraction, failing to exert its optimal biological performance; in addition, its composition is relatively simple, and thus cannot satisfy the requirements for complex signal pathway during the bone repair process; furthermore, toxic chemical crosslinking agents are needed during the use of such collagen, which may easily induce immune and inflammatory responses during implantation. In contrast, the biological tissue matrix material prepared by the present invention, due to the advanced extraction process thereof, can retain the undenatured collagen and other extracellular matrix existing in the tissue to a maximum extent; thus it has rich components, and can better facilitate cell absorption and provide various signals required for cell migration, growth and differentiation; since the extraction process does not destroy the bonds between collagens, the obtained protein is in natural cross-linking state, and no chemical cross-linking agent is needed, the degradation of the biological tissue matrix material is mainly carried out via various enzymes secreted by cells. These properties of the biological tissue matrix material prepared by the present invention determine its great advantages and multiple functions as bone repair substitute material relative to the pure collagen materials.

The composite of biological tissue matrix material of micron size having an intact protein structure with bioceramic also of micron size is realized by the advanced microfabrication technology developed by the present invention. A new composite material for bone regeneration with homogenous distribution of various components, excellent biocompatibility, osteoconductivity and osteoinductivity is prepared. The present invention overcomes the technical drawbacks that other materials have using large size of collagen as substrate, which are difficult to form homogeneous composite materials with bioceramic materials or other polymeric materials due to the size differences thereof. The composite materials for bone repair described in the present invention can be fabricated by mixing the biological tissue matrix microfibers thereof with any bioceramic materials also of micron size to form a composite material with various components homogeneously dispersed therein. Therefore, the composite material does not need to be prepared by relatively complex biological mineralization process, such that industrial production scale-up can be achieved more easily.

The composite material for bone repair prepared by the present invention has a complete three-dimensional porous network structure, without additional physical or chemical cross-linking; the protein components in the biological tissue matrix material maintain a natural triple helix structure; the composite material has excellent biocompatibility, complete biodegradability, superior osteoconductivity, good osteoinductivity and osteogenecity; in the meantime, composite material of the invention has certain mechanical strength and shape memory function, and is a good bone filling material with bioactivity or a repair material for a large area of bone defects.

BRIEF DESCRIPTION OF THE DRAWINGS

FIG. 7 shows the repair of a critical-sized defect of mouse tibia using the microfibrillar biological tissue matrix/calcium hydrophosphate composite material which has a calcium hydrophosphate content (weight) of 60% and is mixed with fresh mouse bone marrow before implantation. (A) is an X-ray image on day 1 after surgery, showing a bone defect of 3.5 millimeter in length in the mouse tibia, (B) is an X-ray image at week 12 after implanting Healos®, (C) is an X-ray image at week 12 after implanting Vitoss® BA, (D) is an X-ray image at week 12 after implanting the biological tissue matrix composite material of the present invention, (E) is a Von Kossa staining image at week 12 after implanting Healos®, (F) is a Von Kossa staining image at week 12 after implanting Vitoss® BA, (G) is a Von Kossa staining image at week 12 after implanting the biological tissue matrix composite material of the present invention.

FIG. 8 shows the repair of a bone non-union of a mouse tibia using the microfibrillar biological tissue matrix/calcium hydrophosphate composite material which has a calcium hydrophosphate content (weight) of 75% and is mixed with fresh mouse bone marrow before implantation. (A) is an X-ray image showing that the pseudarthrosises at both ends of the bone non-union are cut off and the marrow cavities are re-exposed, (B) is an X-ray image at eight weeks after repairing the bone non-union through implanting the composite material which is prepared by the present invention and mixed with fresh mouse bone marrow before implantation, (C) is a micro-computed tomography image at eight weeks after repairing the bone non-union through implanting the composite material which is prepared by the present invention and mixed with fresh mouse bone marrow before implantation, (D) is a Goldner's Trichrome staining image of the newly generated tissue at the original bone non-union site eight weeks after repairing the bone non-union through implanting the composite material which is prepared by the present invention and mixed with fresh mouse bone marrow before implantation, (E) is a Von Kossa staining image of the newly generated tissue at the original bone non-union site eight weeks after repairing the bone non-union through implanting the composite material which is prepared by the present invention and mixed with fresh mouse bone marrow before implantation.

EMBODIMENTS OF THE INVENTION

The present invention will be further described in detail with the following examples, which are intended to illustrate the present invention rather than limit the present invention.

Example 1

240 mg of the microfibrillar biological tissue matrix material obtained by decellularizing porcine skin and sterilizing by gamma ray irradiation was added to 1 ml of deionized water filtered through a 0.22 µm PVDF membrane. The microfibrillar biological tissue matrix was dispersed homogeneously in the water by a vortex mixer. In addition, 360 mg of calcium hydrophosphate powder with particle size of around 25 µm was added into 1 ml of deionized water filtered through a 0.22 µm PVDF membrane. The calcium hydrophosphate was dispersed homogeneously in the water by a vortex mixer. 1 ml suspension of the microfibrillar biological tissue matrix was then mixed with 1 ml suspension of the calcium hydrophosphate. The microfibrillar biological tissue matrix and calcium hydrophosphate were homogenized by a homogenizer (the weight percent of calcium hydrophosphate in the composite material is 60%). The paste of the homogeneously mixed microfibrillar biological tissue matrix and calcium hydrophosphate was transferred into a mold with specific shape for molding, and then frozen at −20° C. for 24 hours, and further freeze dried at −50° C. for 48 hours.

Figure 1:
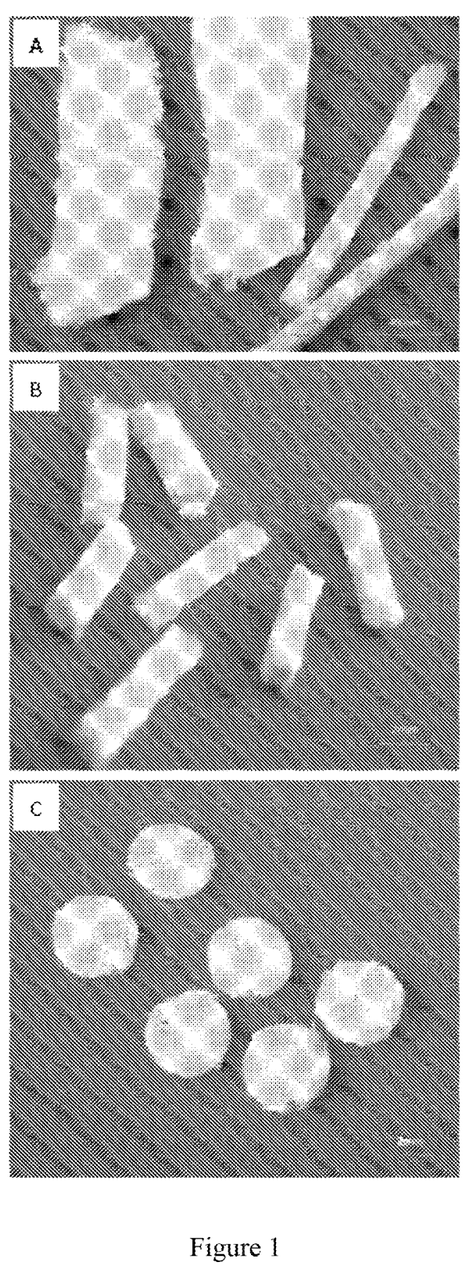
FIG. 1 is the images of some products prepared by the present invention, which respectively are microfibrillar biological tissue matrix/calcium hydrophosphate composite materials of (A) flake and strip shape, (B) columnar shape, and (C) disk shape.
Figure 2:
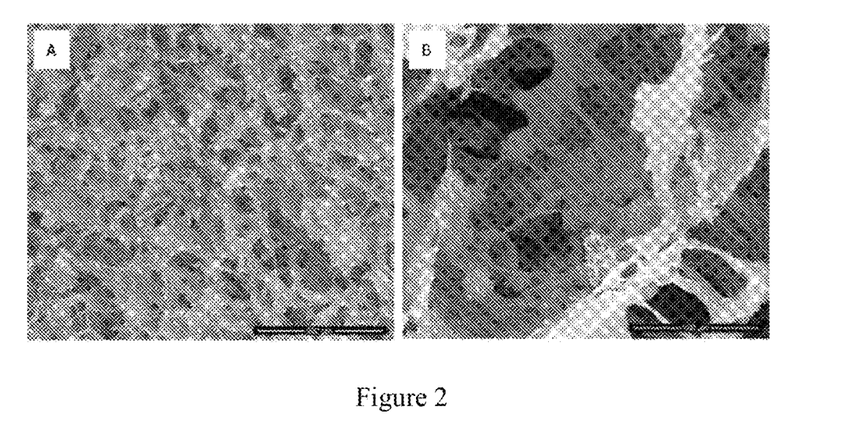
FIG. 2 is the scanning electron microscope images of the microfibrillar biological tissue matrix/calcium hydrophosphate composite material with a calcium hydrophosphate content (weight) of 60% prepared by the present invention. The composite material prepared by the present invention has a three-dimensional porous structure, wherein the calcium hydrophosphate particles are dispersed homogeneously in the continuous phase of the microfibrillar biological tissue matrix.
Figure 3:
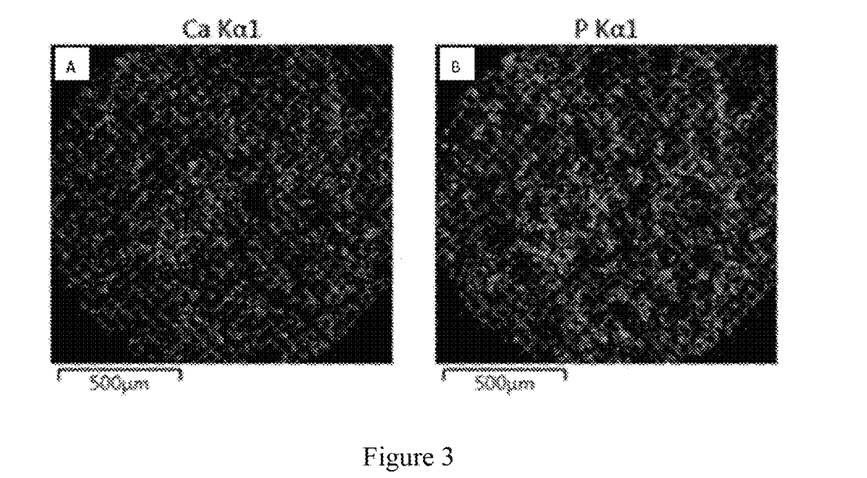
FIG. 3 is the elemental scanning images of (A) calcium and (B) phosphorous in the microfibrillar biological tissue matrix/calcium hydrophosphate composite material prepared by the present invention.

The produced microfibrillar biological tissue matrix/calcium hydrophosphate composite material can be made into various shapes, such as flake, strip, columnar, disk shapes and the like, as shown in FIGS. 1(A), 1(B) and 1(C). The scanning electron microscopic images of the produced microfibrillar biological tissue matrix/calcium hydrophosphate composite material are as shown in FIG. 2. The produced composite material has a three-dimensional porous structure, wherein the calcium hydrophosphate particles are dispersed homogeneously in the continuous phase of microfibrillar biological tissue matrix. FIG. 3 is the elemental scanning images of calcium and phosphorus in the composite material, showing a homogeneous dispersion of calcium hydrophosphate component in the composite material.

Example 2

240 mg of the microfibrillar biological tissue matrix material was weighed, which was obtained by decellularizing porcine skin and sterilized by gamma ray irradiation. 1 ml of deionized water filtered through a 0.22 μm PVDF membrane was added to the biological tissue matrix microfiber material. The microfibrillar biological tissue matrix was dispersed homogeneously in the water using a vortex mixer. In addition, 103 mg of calcium hydrophosphate powder with a particle size of about 25 μm was weighed and added into 1 ml of deionized water filtered through a 0.22 μm PVDF membrane. The calcium hydrophosphate was dispersed homogeneously in the water using a vortex mixer. 1 ml suspension of the microfibrillar biological tissue matrix was then mixed with 1 ml suspension of the calcium hydrophosphate. The microfibrillar biological tissue matrix and calcium hydrophosphate were homogenized by a homogenizer (the weight percent of calcium hydrophosphate in the composite material is 30%). The paste of the homogeneously mixed microfibrillar biological tissue matrix and calcium hydrophosphate was transferred into a mold with specific shape for molding and then frozen in liquid nitrogen for 24 hours, and further freeze dried at −50° C. for 48 hours.

Figure 4:
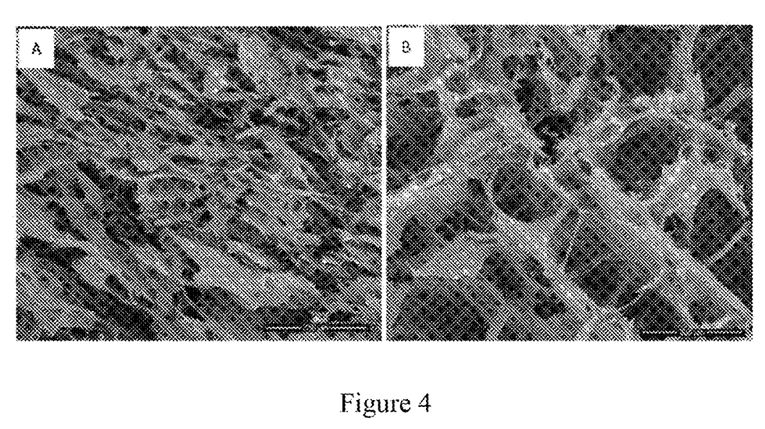
FIG. 4 is the scanning electron microscope images of the microfibrillar biological tissue matrix/calcium hydrophosphate composite material prepared by the present invention at different frozen temperatures. (A) is the scanning electron microscope image of the microfibrillar biological tissue matrix/calcium hydrophosphate composite material obtained by freezing the material in liquid nitrogen at −196° C. and further freeze drying. The pore size of the obtained three-dimensional scaffold material is smaller than that of the composite material prepared by freezing at −20° C. and further freeze drying as shown in (B)

The scanning electron microscopic image of the produced microfibrillar biological tissue matrix/calcium hydrophosphate composite material is shown in FIG. 4(A). The produced composite material has a three-dimensional porous structure, the pore size thereof is smaller than that of the composite material produced by freezing at the condition of −20° C. and then freeze drying in example 1 [FIG. 4(B)].

Example 3

240 mg of microfibrillar biological tissue matrix material was weighed, which was obtained by decellularizing porcine skin and sterilizing by gamma ray irradiation. 1 ml of deionized water filtered through a 0.22 μm PVDF membrane was added to the biological tissue matrix microfiber material. The microfibrillar biological tissue matrix was dispersed homogeneously in the water by a vortex mixer. In addition, 720 mg of calcium hydrophosphate powder with a particle size of about 25 μm was weighed and added into 1 ml of deionized water filtered through a 0.22 μm PVDF membrane. The calcium hydrophosphate was dispersed homogeneously in the water by a vortex mixer. 1 ml suspension of the microfibrillar biological tissue matrix was then mixed with 1 ml suspension of the calcium hydrophosphate. The microfibrillar biological tissue matrix and calcium hydrophosphate were homogenized by a homogenizer (the weight percent of calcium hydrophosphate in the composite material is 75%). The paste of the homogeneously mixed microfibrillar biological tissue matrix and calcium hydrophosphate was transferred into a mold with specific shape for molding, and then frozen at −20° C. for 24 hours, and further freeze dried at −50° C. for 48 hours.

Figure 5:
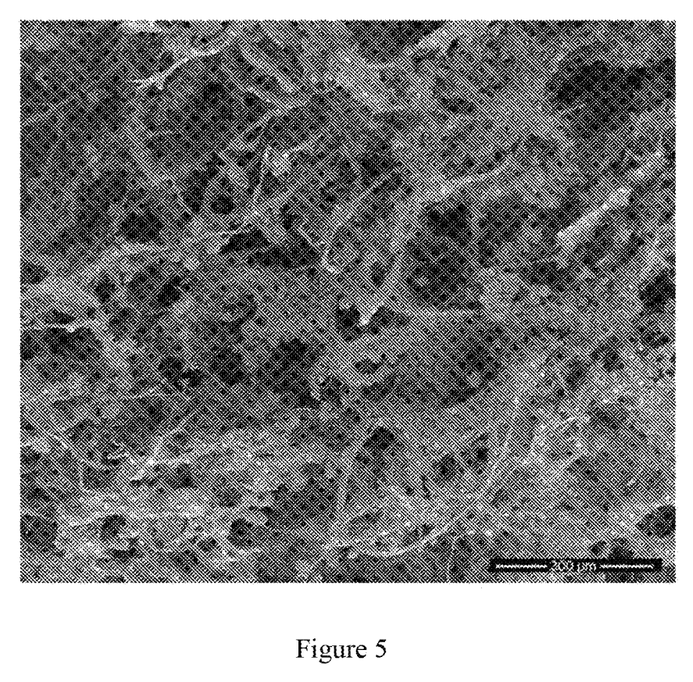
FIG. 5 is the scanning electron microscope image of the microfibrillar biological tissue matrix/calcium hydrophosphate composite material with a calcium hydrophosphate content (weight) of 75% prepared by the present invention.

The scanning electron microscopic image of the produced microfibrillar biological tissue matrix/calcium hydrophosphate composite material is shown in FIG. 5. The produced composite material has a three-dimensional porous structure, wherein the calcium hydrophosphate particles are dispersed homogeneously in the continuous phase of microfibrillar biological tissue matrix. As compared to the composite material with a calcium hydrophosphate content of 60%, the composite material with a calcium hydrophosphate content of 75% has a denser distribution of calcium hydrophosphate particles, and the mechanical strength and operability thereof are both improved.

Example 4

Figure 6:
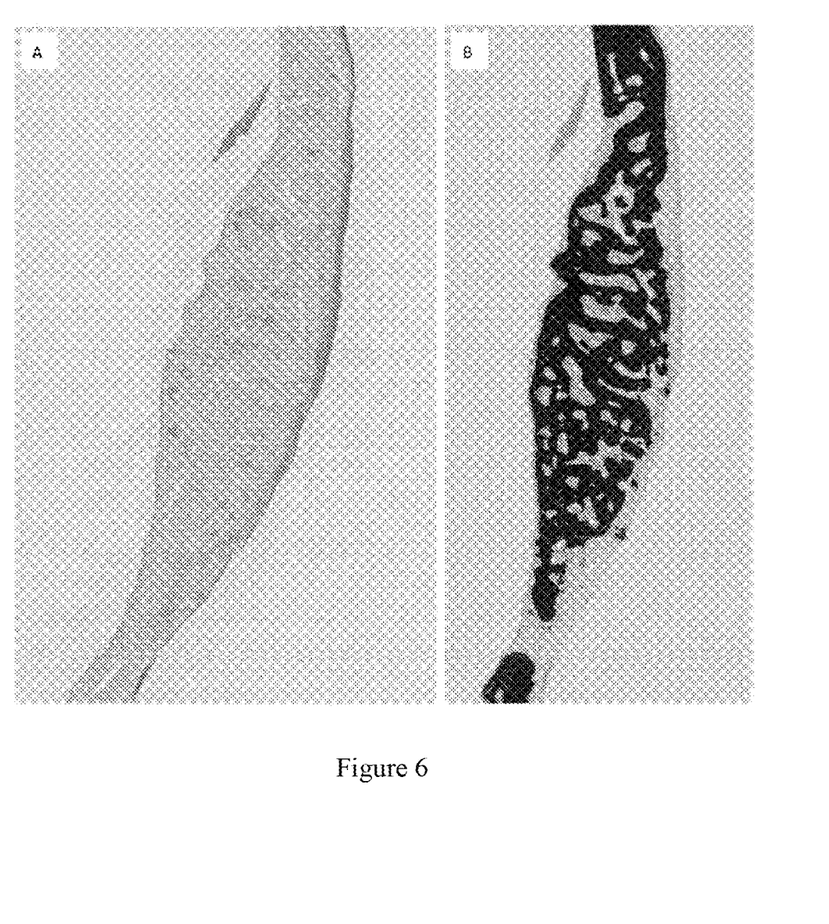
FIG. 6 shows the histological staining images of the implant at 6 weeks after implanting the microfibrillar biological tissue matrix/calcium hydrophosphate composite material into a mouse calvarial defect. The composite material has a calcium hydrophosphate content (weight) of 30% and is mixed with fresh mouse bone marrow before implantation. (A) is Goldner's Trichrome staining, (B) is Von Kossa staining.

A calvarial defect was created by removing a round piece of calvarial bone with a diameter of 15 mm using immune deficient mice. The sterile biological tissue matrix composite material in example 2 (the calcium hydrophosphate content is 30%) was saturated with fresh mouse bone marrow, and implanted into the calvarial defect. After 6 weeks, the mice were sacrificed. The mouse calvaria was removed and fixed in 70% ethanol solution. The tissue at the implant site was embedded in polymethylmethacrylate and then sectioned. New bone formation and bone mineral deposit were observed via Goldner's Trichrome staining and von Kossa staining. The Goldner's Trichrom staining in FIG. 6(A) shows that the implanted biological tissue matrix/calcium hydrophosphate material has been completely absorbed and replaced by the newly generated cancellous bone after 6 weeks. The active osteoblasts continuously generate new bone and the osteoclasts actively participate in bone reconstruction. The von Kossa staining in FIG. 6(B) shows that the original bone defect has been filled with a large amount of bone mineral tissue, and almost the whole bone defect area is filled.

Example 5

Figure 7:
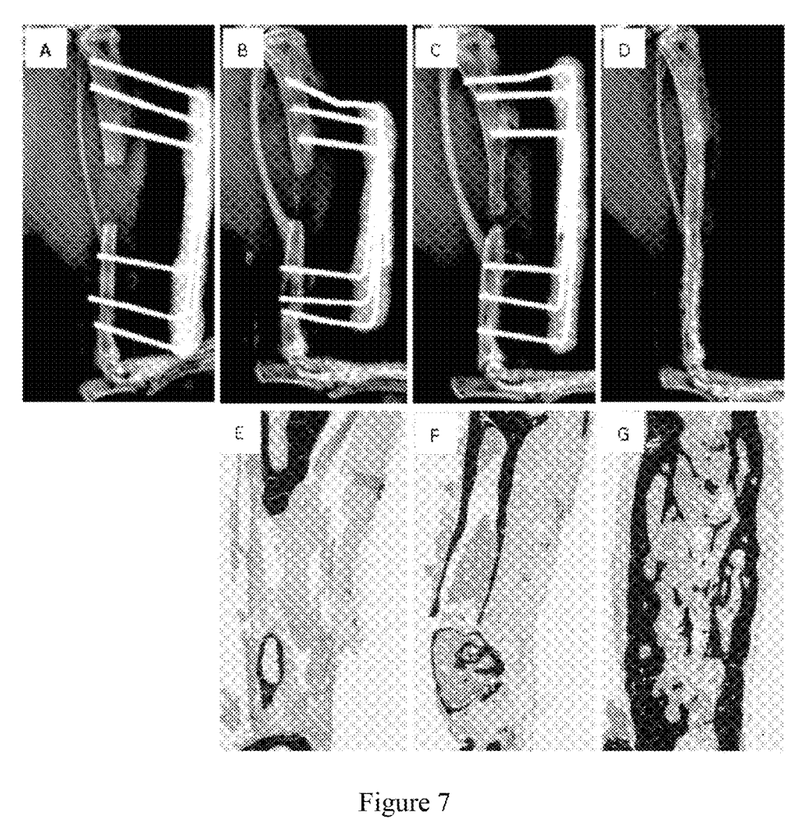

A defect was created by removing a section of bone tissue of about 3.5 mm in length from the tibia of a immune deficient mouse. The sterile biological tissue matrix composite material in example 1 (the calcium hydrophosphate content is 60%) was saturated with fresh mouse bone marrow, and implanted into the bone defect. As experimental controls, Healos® from Johnson & Johnson and Vitoss® BA from Stryker were also saturated with fresh mouse bone marrow and implanted into the bone defect. After 6 weeks, X-ray images show that a large amount of new bone tissue is formed in the mice implanted with the composite material of the present invention. Therefore, the external fixing device was removed to let the mouse continue its recovery. The mice implanted with Healos® or Vitoss® BA only have a small amount of bone tissue formed at the bone defects. Thus, the external fixing devices were kept for fixing the bone defects. After 12 weeks, the mice were sacrificed. The mice tibias were removed and fixed in 70% ethanol solution. The tissue at implant site was embedded into polymethylmethacrylate and then sectioned. New bone formation and bone mineral deposit were observed via Goldner's Trichrome staining and von Kossa staining. FIG. 7(A) is the X-ray image on day 1 after surgery, showing a 3.5 mm bone defect in the mouse tibia. FIGS. 7(B), (C) and (D) respectively are the X-ray images at week 12 after implanting Healos®, Vitoss® BA and the biological tissue matrix composite material of the present invention. The X-ray images show that, after 12 weeks, the mice implanted with Healos® only have limited new bone formation at the bone defect; the mice implanted with Vitoss® BA have some new bone formation at the bone defect, but the newly generated bone tissue fails to repair the bone defect; the bone defect in the mouse implanted with the biological tissue matrix composite material of the present invention has been completely repaired. FIGS. 7(E), (F) and (G) are the von Kossa staining images at week 12 after implanting Healos®, Vitoss® BA and the biological tissue matrix composite material of the present invention, respectively. The images of von Kossa staining show that the mice implanted with Healos® only have limited new bones formation at the bone defect; the mice implanted with Vitoss® BA have some new bone formation at the bone defect, but the newly generated bone tissue fails to repair the bone defect; the bone defect in the mice implanted with the biological tissue matrix composite material of the present invention has been completely repaired, and the newly generated cortical bone perfectly connects the original bone tissue at both ends. The implanted biological tissue matrix/calcium hydrophosphate material has been completely absorbed. The peripheral cortical bone has formed at the original bone defect. The cancellous bone in the marrow cavity is being absorbed by osteoclasts. The reconstruction of the marrow cavity has begun. The results of the experiment show that the bone repair performance of the biological tissue matrix composite material described in the present invention is much better than that of the bone repair materials of Healos® from Johnson & Johnson and Vitoss® BA from Stryker. The biological tissue matrix composite material described in the present invention can induce the bone tissue formation and repair extremely large area of bone defects simply by the composite material per se and fresh bone marrow, without using growth factors and stem cells.

Example 6

Figure 8:
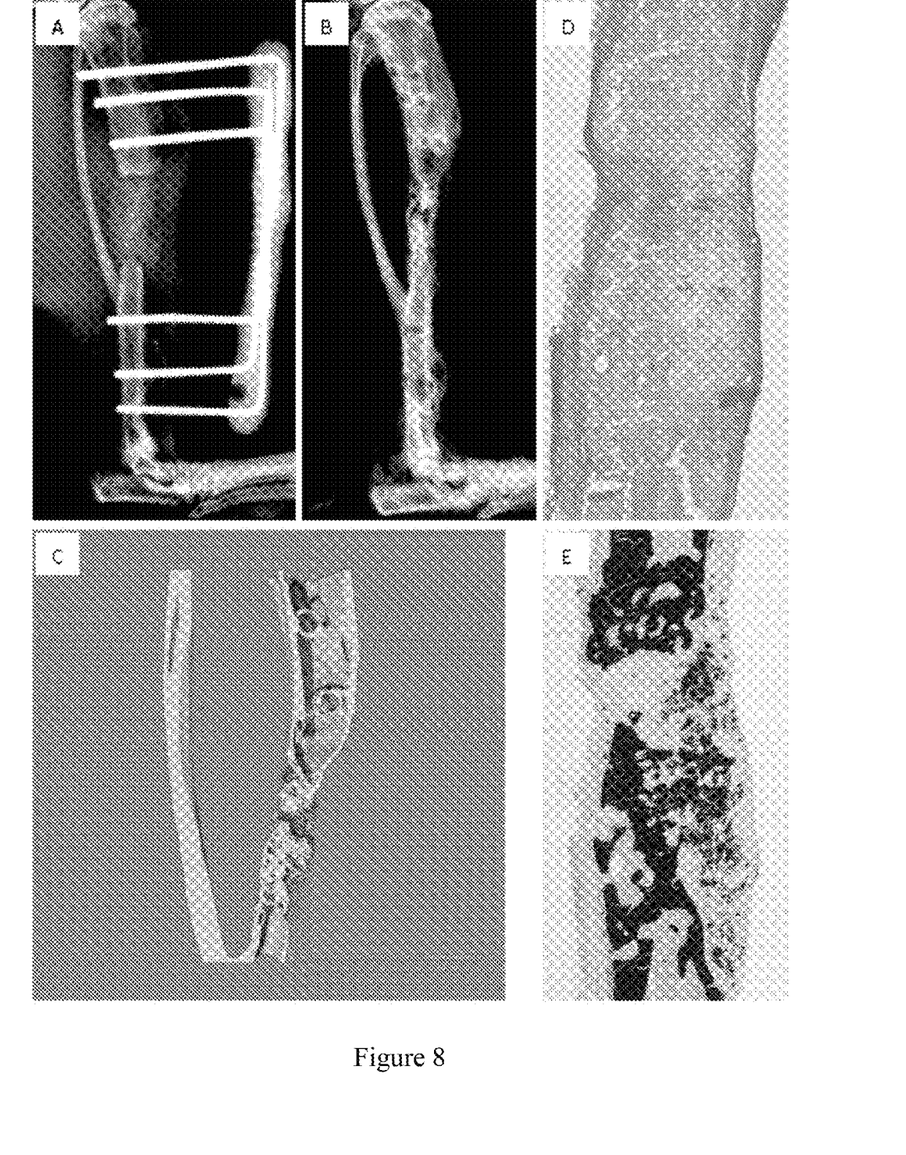

A segmental defect was created by cutting off a section of bone tissue with a length of about 3.5 mm from the tibia of an immune deficient mouse. The defect was fixed with an external fixing device and no material was implanted. The animal was then allowed to recover for 6 weeks after surgery. After 6 weeks, pseudarthrosises were observed to form at both ends of the mouse tibia defect, which is known as bone non-union in the clinic. A subsequent surgery was performed at this time. The pseudarthrosises at both ends of the tibia bone non-union were cut off to expose marrow cavities. The length of the bone defect was about 4 mm at this time. Then, the sterile biological tissue matrix composite material in example 3 (the calcium hydrophosphate content is 75%) was saturated with fresh mouse bone marrow and implanted into the bone defect. After another 8 weeks, the mice were sacrificed. Each mouse tibia was recovered and fixed in 70% ethanol solution. The tissue at the implant site was embedded into polymethylmethacrylate and then sectioned. The new bone formation and bone mineral deposit were observed via Goldner's Trichrome staining and von Kossa staining. FIG. 8(A) is the X-ray image of the bone after cutting the pseudarthrosises and implanting the composite material, showing a bone defect with a length of about 4 mm in the mouse tibia. FIG. 8(B) is the X-ray image at week 8 after implanting the composite material. FIG. 8(C) is the micro-computed tomography image at week 8 after implanting the composite material, which shows a large amount of new bone formation at the position of the original bone non union 8 weeks after implanting the composite material. The Goldner's Trichrome staining in FIG. 8(D) shows that the implanted biological tissue matrix/calcium hydrophosphate material is being gradually absorbed with the for of new bone tissue after 8 weeks. Active osteoblasts generate new bone constantly and the osteoclasts actively participate in the remodeling of the bone. A large amount of cancellous bone forms at the original bone non union, and the presence of cartilage tissue is observed, suggesting that the bone may be formed via endochondral ossification. The von Kossa staining in FIG. 8(E) shows that a large amount of new bone mineral tissue is forming at the original bone non union. The experimental results show that the biological tissue matrix composite material described in the present invention, when combined with fresh bone marrow but without growth factors or stem cells, can induce the bone tissue formation and repair the bone non-union.

Only several specific embodiments in the present invention are illustrated above, which cannot be regarded as limiting the protection scope of the present invention. Any equivalent change or modification made according to the spirit of the present invention should be considered as falling within the protection scope of the present invention.

The invention claimed is:

1. A composite material for bone repair based on decellularized biological tissue matrix material, comprising 10%-90% of a decellularized biological tissue matrix material as organic phase and 90%-10% of a calcium salt as inorganic phase;
   the inorganic phase as a dispersed phase is distributed in form of particles within the organic phase as a continuous phase; the inorganic phase can be distributed homogeneously in the organic phase, or be distributed with a certain gradient in the organic phase; and
   the decellularized biological tissue matrix material has a microfibrillar shape, and the microfibrillar decellularized biological tissue matrix material has a diameter of 1-250 micrometers and a length of 100-4000 micrometers.

2. The composite material for bone repair based on decellularized biological tissue matrix material according to claim 1, wherein the calcium salt is replaced by bioglass, bioceramic, mineral containing strontium, zinc, magnesium or silicon, or salt containing strontium, zinc, magnesium or silicon as the inorganic phase.

3. The composite material for bone repair based on decellularized biological tissue matrix material according to claim 1, having a three-dimensional porous network structure.

4. The composite material for bone repair based on decellularized biological tissue matrix material according to claim 1, wherein the decellularized biological tissue matrix material derives from soft tissue of mammals, the soft tissue of mammals includes a soft tissue of pig, a soft tissue of bovine and a soft tissue of human body; the soft tissue includes skin, dermis, blood vessel, diaphragm, muscle tendon, ligament, large intestine, small intestine and nervous tissue.

5. The composite material for bone repair based on decellularized biological tissue matrix material according to claim 1, wherein the calcium salt is hydroxyapatite, α-tricalcium phosphate, β-tricalcium phosphate, calcium hydrophosphate, calcium hydrophosphate dihydrate, calcium dihydrogenphosphate, tetracalcium phosphate, octacalcium phosphate, calcium sulfate or calcium carbonate.

6. A preparation method of the composite material for bone repair according to claim 1, characterized in that it comprises the following steps:
   8.1) preparing a microfibrillar decellularized biological tissue matrix material, comprising the following steps:
      (a) collecting raw tissue material, rinsing off blood, cutting into desired size, and preserving the material at a low temperature of 2-10° C.;

(b) disinfecting and sterilizing: sterilizing the raw tissue material in a disinfectant solution, washing sufficiently with sterile deionized water, and then rinsing with a sterile physiological saline;

(c) cutting: cutting the raw tissue material into a desired size, so as to facilitate tissue smashing and decellularization;

(d) smashing the tissue: smashing and homogenizing the disinfected raw tissue material by a grinder;

(e) soaking the material in a series of decellularization solutions to remove cells, and degrading the remaining desoxyribonucleic acid with deoxyribonuclease solution;

washing the tissue matrix: washing the product in step (e) by physiological saline with a mass concentration of 0.9%, and removing the supernatant obtained via the treatment of step (e) by centrifugation process;

(g) terminally sterilizing: dispersing the product in step (f) into a solvent of a physiological saline or a phosphate buffer saline in a concentration of 10-40 mg/ml, sterilizing, and sealing the obtained decellularized biological tissue matrix microfibers in a closed container to preserve;

8.2) preparing bioceramic microparticles, comprising the following steps:

(h) obtaining bioceramic microparticles with a particle size of 1-500 micrometers after steps of mechanical pulverization, high-rate ball-milling, and sieving of the bioceramics according to specific application, and then disinfecting and sterilizing the bioceramic microparticles under high temperature and high pressure to inactivate virus;

(i) mixing the bioceramic microparticles with sterile physiological saline, sufficiently stirring and shocking to obtain a homogeneous suspension with a concentration of 500-1000 mg/ml;

8.3) preparing a composite material for bone repair, comprising the following steps:

(j) physically mixing the microfibrillar decellularized biological tissue matrix material obtained in (g) of step 8.1) with the sterile particulate bioceramic obtained in (i) of step 8.2) homogeneously according to the ratio defined in claim 1, to obtain a mixture of composite material in a fluid state;

(k) transferring the mixture of composite material in (j) of step 8.3) into a mold, placing the mold filled with the composite materials at a temperature of −20° C. to −196° C. for 1-24 hours to obtain a frozen mixture;

(l) removing the solvent from the mixture at a frozen state obtained in (k) of step 8.3) at a low temperature of −20° C. to 10° C. and under a vacuum environment of 10-2000 millitorr for 12-96 hours, obtaining a three-dimensional porous composite material for bone repair;

(m) terminally sterilizing the composite material for bone repair obtained in (l) of step 8.3).

7. A preparation method of the composite material for bone repair according to claim 1, characterized in that it comprises the following steps:

9.1) preparing a microfibrillar decellularized biological tissue matrix material according to the step 8.1) defined in claim 6;

9.2) preparing the composite material for bone repair, comprising the following steps:

(a) transferring the decellularized biological tissue matrix material in step 9.1) into a mold, placing the mold filled with the material at a temperature of −20° C. to −196° C. for 1-24 hours to obtain a frozen biological tissue matrix material;

(b) removing the solvent from the biological tissue matrix material at a frozen state obtained in (a) of step 9.2) at a low temperature of −20° C. to 10° C. and under a vacuum environment of 10-2000 millitorr for 12-96 hours, obtaining a three-dimensional porous biological tissue matrix material;

(c) soaking the three-dimensional porous biological tissue matrix material obtained in (b) of step 9.2) in a solution containing calcium ion at 20-37° C. for 1-4 hours, then taking out the biological tissue matrix material, and washing with deionized water three times, each time for 5 minutes; soaking the biological tissue matrix material in a solution containing phosphate ion at 20-37° C. for 1-4 hours, then taking out the biological tissue matrix material, and washing with deionized water three times, each time for 5 minutes; the molar ratio of the addition amount of the calcium ion to that of the phosphate ion is Ca/P=1/1 to 2/1; repeating the above steps 5 times to obtain a three-dimensional porous composite material for bone repair; terminally sterilizing the composite material for bone repair obtained in (c) of step 9.2).

8. The preparation method of the composite material for bone repair according to claim 6, characterized in that raw material derives from soft tissue of mammals, the soft tissue of mammals includes a soft tissue of pig, a soft tissue of bovine and a soft tissue of human body, and the soft tissue includes skin, dermis, blood vessel, diaphragm, muscle tendon, ligament, large intestine, small intestine and nervous tissue.

9. The preparation method of the composite material for bone repair according to claim 7, characterized in that raw material derives from soft tissue of mammals, the soft tissue of mammals includes a soft tissue of pig, a soft tissue of bovine and a soft tissue of human body, and the soft tissue includes skin, dermis, blood vessel, diaphragm, muscle tendon, ligament, large intestine, small intestine and nervous tissue.

* * * * *